United States Patent [19]
Kressner et al.

[11] Patent Number: 5,604,329
[45] Date of Patent: Feb. 18, 1997

[54] HOUSING, IN PARTICULAR FOR AN ELECTRICAL TOOTH CLEANING DEVICE, AND PROCESS FOR PRODUCING IT

[75] Inventors: Gerhard Kressner, Altenstadt; Peter Hartwein, Kronberg; Georg Spiekermann, Salzburg, all of Germany

[73] Assignee: Braun Aktiengesellschaft, Kronberg, Germany

[21] Appl. No.: 398,061

[22] Filed: Mar. 3, 1995

[30] Foreign Application Priority Data

Mar. 9, 1994 [DE] Germany ............... 44 07 782.3

[51] Int. Cl.⁶ .................................................. H01L 23/28
[52] U.S. Cl. ............... 174/52.2; 264/297.2; 264/328.1; 174/65 R
[58] Field of Search ............... 174/52.1, 52.2, 174/65 R; 15/1, 167.1, DIG. 1; 264/328.1, 297.2, 297.7

[56] References Cited

U.S. PATENT DOCUMENTS

| | | | |
|---|---|---|---|
| 3,143,696 | 8/1964 | Springer | 318/266 |
| 3,939,393 | 2/1976 | Nagasaki et al. | 174/52.2 X |
| 4,600,969 | 7/1986 | Hendrickson et al. | 174/52.2 X |
| 4,899,257 | 2/1990 | Yamamoto | 29/841 X |
| 4,972,975 | 11/1990 | Fuhrig | 222/182 |
| 5,010,212 | 4/1991 | Sumi et al. | 174/52.2 |
| 5,196,651 | 3/1993 | Pageaud et al. | 174/52.1 |
| 5,293,002 | 3/1994 | Grenet et al. | 174/52.2 |
| 5,378,153 | 1/1995 | Giuliani et al. | 15/167.1 X |

FOREIGN PATENT DOCUMENTS

| | | |
|---|---|---|
| 0125619 | 11/1984 | European Pat. Off. . |
| 1414679 | 9/1965 | France . |
| 1258981 | 1/1968 | Germany . |
| 8116313 U | 11/1982 | Germany . |
| 120993 | 8/1989 | Japan . |

*Primary Examiner*—Bot L. Ledynh
*Attorney, Agent, or Firm*—Fish & Richardson, P.C.

[57] ABSTRACT

A housing (1) for an electrical device for bodycare, in particular for a tooth cleaning device, is described in which electrical components (8), in particular a charger, surrounded by a casting compound (14) are arranged. The components (8) are connected by an electrical cable (10) which is placed through a cable orifice in the housing (1). The cable orifice (11) is arranged in an external wall (12) of the housing (1) and represents the only orifice in the housing (1) to the electrical components (8). To produce the housing (1), the casting compound (14) is introduced through the cable orifice (11) into the housing (1) by means of a loading device (13).

13 Claims, 2 Drawing Sheets

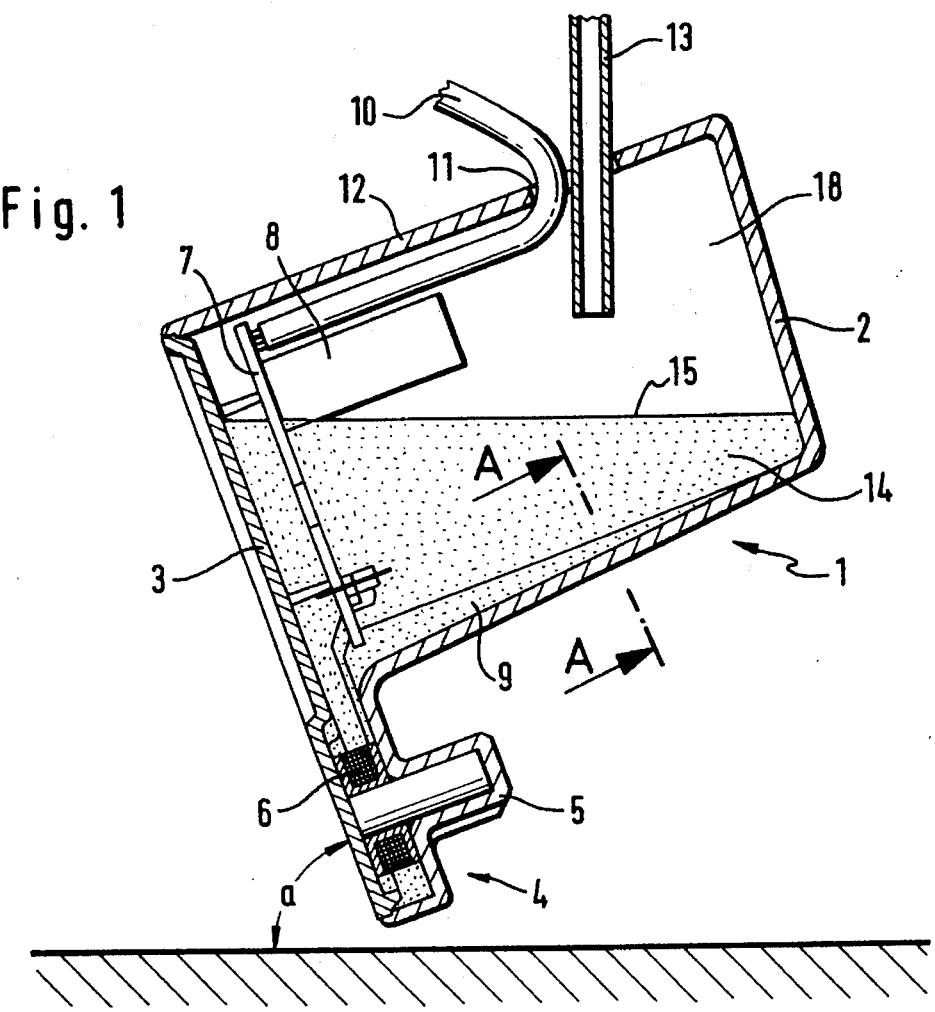
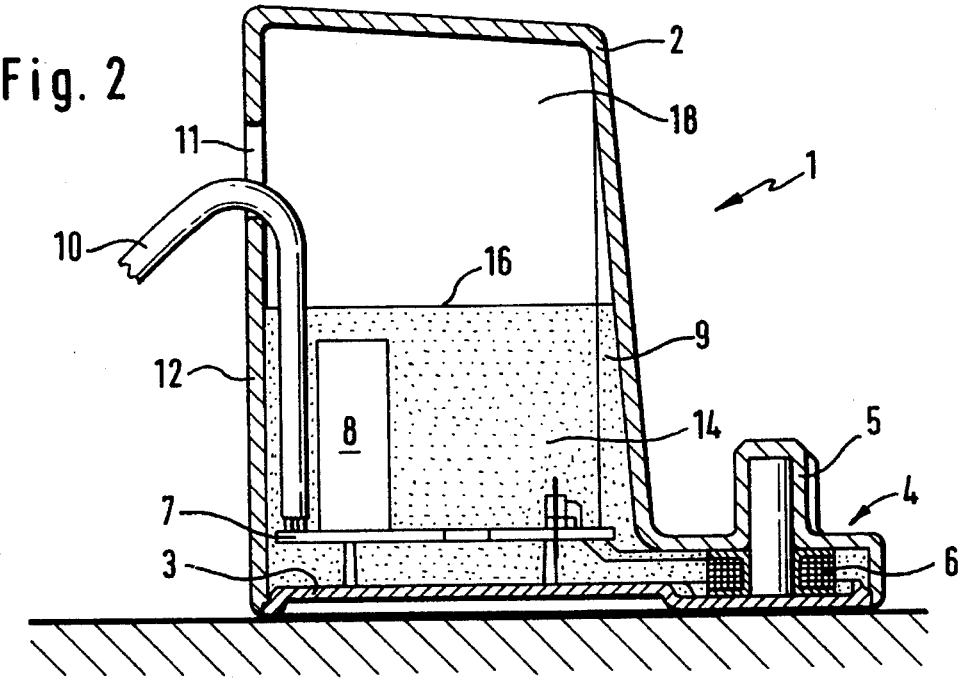

HOUSING, IN PARTICULAR FOR AN ELECTRICAL TOOTH CLEANING DEVICE, AND PROCESS FOR PRODUCING IT

The invention relates to a housing for an electrical device for body care, in particular for a tooth-cleaning device, in which there are arranged electrical components which are surrounded by a casting compound and are connected to an electrical cable placed through a cable orifice in the housing.

A housing of this type is known from commercially available electrical tooth-cleaning devices produced by the applicants. In these devices, the housing is provided with a cable stowing space which is divided from the region with the electrical components by a partition wall. The partition wall contains two orifices, the electrical cable connected to the electrical components being placed through one of the orifices. The other orifice serves for loading the casting compound into the region with the electrical components during production of the housing. For this purpose, a loading device is inserted into this orifice so the liquid casting compound can flow into the interior of the housing and can surround the electrical components. After the casting compound has been loaded, the loading device is removed again and the housing is set aside for the curing of the casting compound. The orifice in the partition wall remains without having a further use.

An object of the invention is to provide a housing, in particular for an electrical tooth cleaning device, and a process for producing it which is improved with respect to the material required and the necessary production stages.

The object is achieved in that the cable orifice is arranged in an external wall of the housing and represents the single orifice in the housing to the electrical components.

According to the invention, the cable orifice is no longer provided in a partition wall but directly in the external wall of the housing. A partition wall or the like is no longer provided. The function of the partition wall, that is the separation of the electrical components from the cable stowing space, is adopted by the loaded casting compound. The resultant saving in material and reduction in the necessary production stages is obvious.

A further advantage is that the casting compound surrounds not only the electrical components but at least some of the electrical cable. The tension in the electrical cable is therefore reduced so it is not necessary to take further measures in this respect.

Furthermore, only a single orifice to the electrical components, namely said cable orifice, is provided according to the invention. This obviously also represents an improvement, in particular with respect to production of the housing according to the invention.

The electrical cable can be introduced or removed through this cable orifice into the cable stowing space located behind it, as required. The cable stowing space has the advantage that, apart from the cable orifice, it is closed all round and is formed internally by substantially smooth faces. The electrical cable is protected and spared in this way.

In an advantageous development of the invention, when the housing is vertical, the casting compound has a surface which is arranged either substantially horizontally or at an angle of inclination to the horizontal. With the last-mentioned alternative, in particular, that is with an inclined surface of the casting compound, it is possible, on the one hand, for the electrical components to be completely surrounded by the casting compound and therefore insulated but on the other hand for a smaller quantity of casting compound than hitherto to be required in the interior of the housing. This has the advantage that not only the material requirement is smaller but also that the cable stowing space is greater.

In an advantageous embodiment of the invention, supporting ribs which are at least partially coated with casting compound are provided in the interior of the housing. The coating of the supporting ribs with casting compound has the advantage that the electrical cable cannot be damaged by the supporting ribs.

It is particularly desirable if the electrical device for bodycare contains a re-chargable accumulator and the electrical components belong to an electrical charger. In the case of an electrical tooth-cleaning device, a user can use a hand-held device with a rotating bristle member separately from the mains voltage. For charging the accumulator contained in the hand-held device, the hand-held device has to be connected to the charger. This can be carried out, for example, by means of electric contacts or the like, the necessary charger being arranged in the housing according to the invention.

With a process of the type mentioned at the outset, said object is achieved in that the casting compound is introduced into the housing through the cable orifice by means of a loading device.

According to the invention, therefore, the cable orifice has a double function. On the one hand, it serves as an orifice for the electrical cable. On the other hand, however, the casting compound is also loaded through the cable orifice into the interior of the housing. For this purpose the loading device is introduced into the cable orifice when the electrical cable is put through and the liquid casting compound is introduced into the interior of the housing. Once the necessary quantity of casting compound is introduced, the loading device is removed again and the casting compound can solidify. The surface of the solidified casting compound then forms one of the faces of the cable stowing space. The electrical cable placed through the cable orifice and connected to the electrical components also sinks into this surface.

In an advantageous embodiment of the invention, for loading the casting compound, the housing is brought, by means of a conveyor, into a loading position having a loading angle relative to the horizontal. The loading of the casting compound into the interior of the housing is substantially simplified in this way.

In an advantageous development of the invention, for curing of the casting compound, the housing is brought by means of the conveyor, either into a substantially horizontal position or into a position having an angle of inclination to the horizontal. In this way, either the horizontal surface of the casting compound is produced or the surface arranged beneath the angle of inclination.

It is advantageous if the housing is set on a corresponding oblique plane. The respectively desired angle of inclination for loading the casting compound or for curing the casting compound can therefore be produced in a particularly simple manner in terms of the process. For this purpose, the conveyor with the housing is conveyed up or down only said oblique plane and is set on the oblique plane for the loading or curing of the casting compound.

Further features, advantages and possible applications of the invention will emerge from the following description of embodiments which are shown in detail in the drawings. All described and/or illustrated features, individually or in any combination, form the subject of the invention regardless of whether they are combined in the claims or are referred back.

FIG. 1 is a schematic view of a housing of an electrical tooth cleaning device in a sectional side view in which casting compound has been loaded into the interior of the housing by means of a loading device.

FIG. 2 is a schematic view of the housing in FIG. 1 in a sectional side view which has been set in a horizontal position for curing of the casting compound in a first embodiment.

Figure 3:
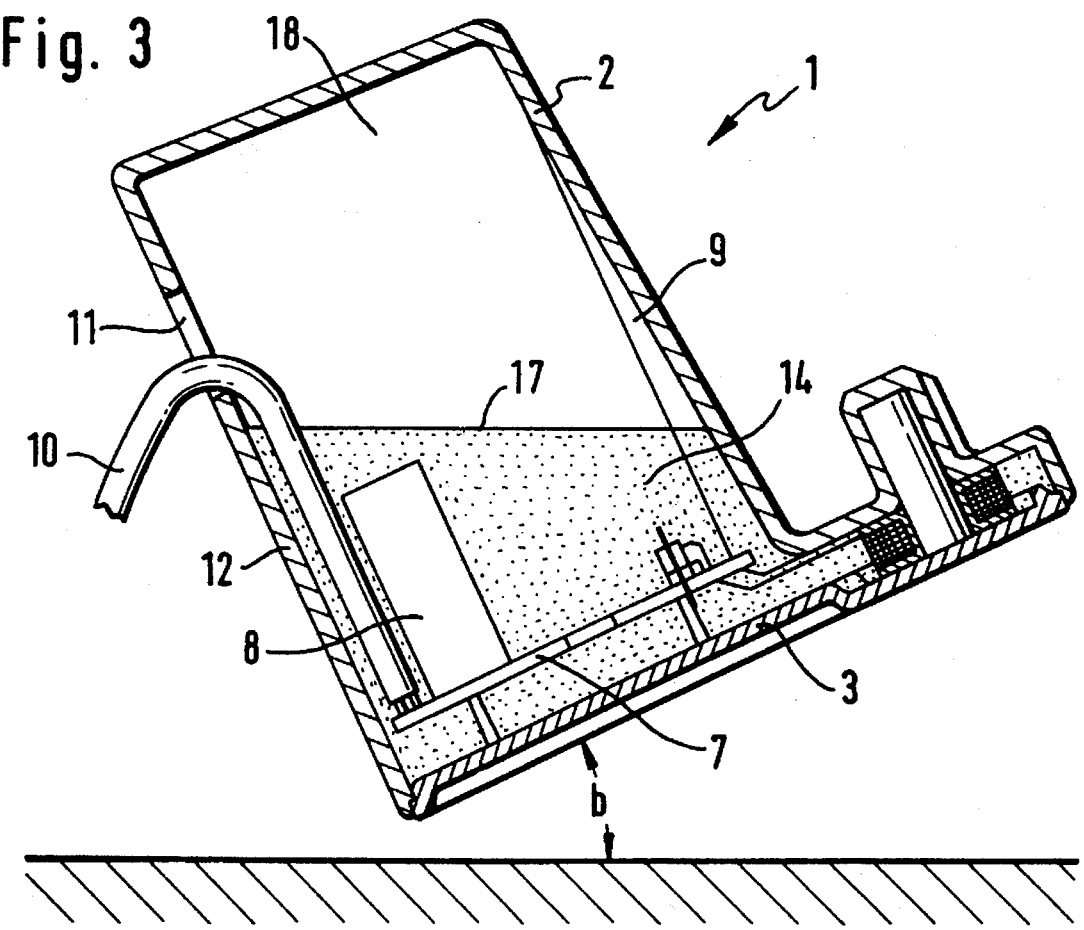
FIG. 3 is a schematic view of the housing in FIG. 1 in a sectional side view which has been set in an inclined position for curing of the casting compound in a second embodiment.

FIG. 1 shows a housing 1 for an electrical tooth cleaning device. The housing 1 is essentially composed of a substantially beaker-shaped upper part 2 and a substantially plane base 3 associated with the orifice in the upper part 2. On one side, the upper part 2 is provided with a projecting supporting member 4 starting from one edge of its beaker shape. The base 3 extends into the region of the support member 4 and completely closes the orifice of the beaker-shaped upper part 2 and the support member 4. A nozzle 5 with a round cross section pointing substantially in the same direction as the beaker shape of the upper part 2 projects from the supporting member 4.

If the housing 1 stands on the base 3 or is fastened in this position in a different way, the nozzle 5 points substantially vertically upwardly and the base 3 extends substantially horizontally. This enables a hand-held device pertaining to the electrical tooth-cleaning device to be placed with an associated recess on the nozzle 5.

The hand-held device contains an electric motor which is driven by an accumulator. The bristles of a bristle member can be set into rotation by the electric motor. A user can therefore clean his teeth by means of the rotating bristles of the hand-held device when the hand-held device is removed.

In order to recharge the accumulator, the user has to place the hand-held device on the nozzle 5 of the housing 1. Electrical energy is then transmitted to the hand-held device by inductive transmission. Appropriate means are provided in the hand-held device and in the housing 1 for this purpose, including a coil 6 in the housing 1.

A printed circuit board 7 extending substantially over the entire orifice of the beaker-shaped upper part 2 is arranged substantially parallel to the base 3 in the housing 1. A number of electrical components 8 is arranged on the printed circuit board 7 and rigidly soldered to the printed circuit board 7. These electrical components 8 are, for example, electrical resistors, capacitors, transistors, etc. Overall, the electrical components 8 form an electrical charger for recharging the accumulator in the above-mentioned hand-held device.

The printed circuit board 7 with the electrical components 8 is fixed within the housing 1 by means of supporting ribs 9. The supporting ribs 9 project from the upper part 2 and extend substantially in the same direction as the beaker shape of the upper part 2.

The height of the upper part 2 is selected to provide a free space, which will be described in detail, above the electrical components 8.

An electrical cable 10 is rigidly connected to the printed circuit board 7 and serves to supply electric energy, for example in the form of a mains voltage, to the charger so the printed circuit board 7 and the electrical components 8 carry current in the connected state.

The electrical cable 8 is guided through a cable orifice 11 out of the housing 1. The cable orifice 11 is arranged in an external wall 12 of the beaker shape of the upper part 2, more specifically in the region of the free space in the upper part 2 which is to be described. The edge of the cable orifice 11 is externally and internally markedly rounded so there are no sharp or pointed edges.

During production of the housing 1, the printed circuit board 7 with the electrical components 8 including the coil 6 and other means for inductive transmission is introduced into the upper part 2. The electrical cable 10 is placed through the cable orifice 11. The upper part 2 is then firmly closed by means of the base 3.

The housing 1 is now brought into a loading position, as shown in FIG. 1. In this loading position, the housing 1 has a loading angle a to the horizontal which is about 70 degrees to 80 degrees in the embodiment described. This loading angle a is selected such that the cable orifice 11 is located in a substantially horizonal position.

In the lower part of FIG. 1, the horizontal is shown as a line so the loading angle a is located, for example, between this line and the base 3.

In terms of the process the loading angle a is achieved in that the housing 1 is held on a conveyor with which the housing 1 is conveyed from one station to the next station of the production plant and in that this conveyor together with the housing 1 has to be moved up or down a corresponding oblique plane. Once the housing 1 is located on the oblique plane, the conveyor is stopped and the loading position is reached.

In the loading position the housing 1 is allocated a loading device 13 which can be, for example, a tubular loading nozzle. The loading device 13 is now introduced into the cable orifice 11. A liquid casting compound 14 is then loaded into the interior of the housing 1 by means of the loading device 13. The quantity of casting compound 14 to be loaded is selected in such a way in the present embodiment that the interior of the housing 1 is substantially half filled with casting compound 14. The loading device 13 is then removed again.

The horizontal surface of the loaded casting compound 14 in the loading position, that is with the housing 1 inclined, is identified by reference numeral 15 in FIG. 1.

In a first embodiment, the housing 1 is brought into a substantially horizontal position after being loaded with the still liquid casting compound 14, as shown in FIG. 2. The horizontal is indicated by a line in the lower part of FIG. 2. The surface of the loaded casting compound 14 is identified by reference numeral 16 in FIG. 2. This surface 16 is arranged substantially parallel to the base 3, and the electrical components 8 including the printed circuit board 7 are located in the region of the housing 1 filled with the casting compound 14.

In a second embodiment which is shown in FIG. 3, the housing 1 is brought into an inclined position after being filled with the still liquid casting compound 14. In this curing position, the housing 1 has an angle of inclination b to the horizontal which is about 40 degrees to 50 degrees in the embodiment described. In the lower part of FIG. 1, the horizontal is drawn in as a line so the angle of inclination b is located, for example, between this line and the base 3. The surface of the loaded casting compound 14 is indicated by reference numeral 17 in FIG. 3. The high electrical components 8 are arranged on the printed circuit board 7 in such a way that they do not project beyond the surface 17. In the present embodiment, the high electrical components 8 are arranged according to FIG. 3 in the left-hand region of the printed circuit board 7 so the casting compound 14 can have a lower height in the right-hand region. The printed circuit board 7 and the electrical components 8 arranged thereon are therefore located completely in the region of the housing 1 filled by the casting compound 14.

In the two embodiments described, the housing 1 is set in the positions shown in FIGS. 2 and 3. The liquid casting compound 14 can now cool and therefore solidify and cure. In the final analysis, this produces a rigid casting compound 14 with the surfaces 16 and 17 shown in FIGS. 2 and 3. The casting compound 14 serves to insulate the printed circuit board 7 and electrical components 8.

In terms of the process, the desired curing position is achieved in the two described embodiments in that the housing 1 is moved over a corresponding plane by the conveyor and is then set aside. In the embodiment according to FIG. 2, the conveyor with the housing 1 is set on a horizontal plane and in the embodiment according to FIG. 3 on an oblique plane having the angle of inclination b to the horizontal.

The aforementioned free space is produced in the interior of the upper part 2 in both embodiments described in FIGS. 2 and 3. This free space represents a cable stowing space 18 into which the electrical cable 10 can be introduced or removed through the cable orifice 11.

Figure 4:
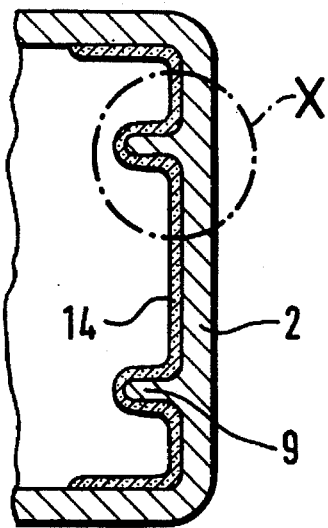
FIG. 4 is a schematic view of the housing in FIG. 1 in a sectional plan view along plane A—A in FIG. 1.
Figure 5:
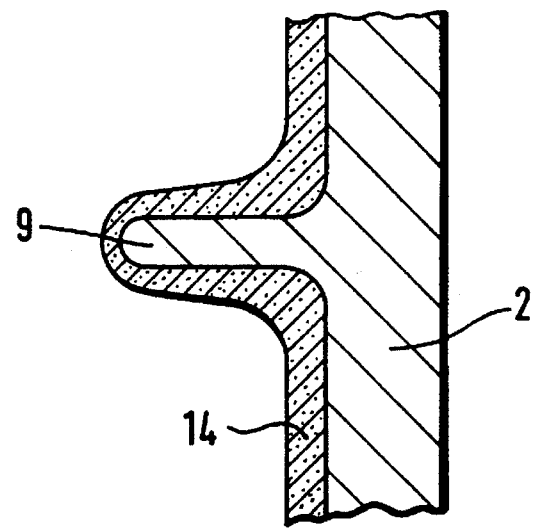
FIG. 5 is a schematic view of the housing in FIG. 1 in a sectional enlargement of detail X in FIG. 4.

FIGS. 4 and 5 show the supporting ribs 9. As shown in FIG. 1, the supporting ribs 9 are completely surrounded by the casting compound 14 during the loading of the liquid casting compound 14. As a result, the supporting ribs 9 retain a thin layer of the casting compound 14 even after the housing 1 has been tilted back from the loading position into the curing position. Owing to the surface tension of the liquid casting compound 14, this produces an irregular thickness in the layer of casting compound 14 located on the supporting ribs 9. This in turn means that the height of the supporting ribs 9 becomes smaller and the radii of the supporting ribs 9 to the surfaces of the housing 1 become greater. Therefore, the supporting ribs 9 have no sharp or pointed edges.

What is claimed is:

1. An electrical device for a body care device comprising a housing having a cable orifice formed in an external wall thereof and leading into an interior cavity of the housing, electrical components arranged within said housing, a casting compound within said housing and surrounding the electrical components, an electrical cable passing through the cable orifice in the housing and connected to the electrical components, wherein the cable orifice represents the only cable orifice in the housing through which connection to the electrical components is made and wherein said casting compound only partially fills the interior of said housing thereby leaving an unfilled portion of the housing that serves as a cable stow space and at least one wall of the cable stow space is defined by a surface of the casting compound.

2. The electrical device according to claim 1, wherein when the housing is vertical, the surface of the casting compound is arranged substantially horizontally.

3. The electrical device according to claim 2, wherein when the housing is vertical, the surface of the casting compound is arranged at an angle of inclination (b) to the horizontal.

4. The electrical device according to one of claims 1 to 3, further comprising supporting ribs in the interior of the housing, said supporting ribs being at least partially coated with the casting compound.

5. The electrical device according to claim 4, wherein the electrical components include an electrical charger for a re-chargeable accumulator.

6. A process for producing the electrical device according to claim 1 comprising loading the casting compound into the housing through the cable orifice by means of a loading device.

7. The process according to claim 6, further comprising in preparation for loading the casting compound, bringing the housing by means of a conveyor, into a loading position having an angle of inclination (a) to the horizontal, wherein (a) is greater than about 70°.

8. The process according to claim 6, further comprising for curing the casting compound, bringing the housing into a substantially horizontal position by means of the conveyor.

9. The process according to claim 6, further comprising for curing the casting compound, bringing the housing by means of the conveyor, into a position having an angle of inclination (b) to the horizontal.

10. The process according to claim 7, wherein the step of bringing the housing into the loading position having an angle of inclination (a) is accomplished by setting the housing on a corresponding oblique plane.

11. The process according to claim 7, further comprising for curing the casting compound, bringing the housing into a substantially horizontal position by means of the conveyor.

12. The process according to claim 7, further comprising for curing the casting compound, bringing the housing by means of the conveyor, into a position having an angle of inclination (b) to the horizontal.

13. The process according to claim 9, wherein the step of bringing the housing into a position having an angle of inclination (b) is accomplished by setting the housing on a corresponding oblique plane.

* * * * *